(12) United States Patent
Nawata et al.

(10) Patent No.: US 7,211,072 B2
(45) Date of Patent: May 1, 2007

(54) WAIST BELT FOR SUPPORTING DISPOSABLE ABSORBENT ASSEMBLIES AND ABSORBENT ARTICLES COMPRISING THE SAME

(75) Inventors: Noriko Nawata, Kobe Hyogo (JP); Yukio Heki, Kobe Hyogo (JP); Hiroyuki Ueno, Kakogawa Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 171 days.

(21) Appl. No.: 10/768,949

(22) Filed: Jan. 30, 2004

(65) Prior Publication Data

US 2004/0186456 A1 Sep. 23, 2004

Related U.S. Application Data

(60) Provisional application No. 60/444,272, filed on Jan. 31, 2003.

(51) Int. Cl.
*A61F 13/15* (2006.01)

(52) U.S. Cl. ................ 604/392; 604/353; 604/385.03; 604/386

(58) Field of Classification Search ................ 604/353, 604/385.03, 386, 387, 392, 394, 400–402
See application file for complete search history.

(56) References Cited

U.S. PATENT DOCUMENTS 1,475,895 A * 11/1923 Stein .......................... 604/400
2,017,499 A * 10/1935 Hower ........................ 604/402
2,092,409 A * 9/1937 Solar .......................... 604/402
2,554,684 A * 5/1951 Rosen ......................... 604/402
D164,840 S * 10/1951 Blumenfeld ................. D2/627

(Continued)

FOREIGN PATENT DOCUMENTS

WO      WO 90/04375 A1    5/1990
WO      WO 91/08725 A1    6/1991

OTHER PUBLICATIONS

Search report for WO 2004/069122 A1, Nawata et al., WIPO, Aug. 2004.*
PCT International Search Report dated Jul. 19, 2004.

*Primary Examiner*—Tatyana Zalukaeva
*Assistant Examiner*—Michael G Bogart
(74) *Attorney, Agent, or Firm*—Gary J. Foose; David M. Weirich; Ken K. Patel

(57) ABSTRACT

A waist belt used for supporting a disposable absorbent assembly is disclosed. The belt includes a central segment positioned along the longitudinal centerline of the belt, at least two intermediate segments transversely outwardly extending from the central segment, and at least two distal segments transversely outwardly extending from an intermediate segment. Each intermediate segment covers a side hip of the wearer when the belt is worn. The longitudinal length of each intermediate segment is greater than that of the central segment, and greater than that of each distal segment. The belt further includes a fastener element positioned on at least one of the distal segments for releasably securing the belt around the waist of the wearer, and an attachment surface formed at least on each intermediate segment for releasably attaching the disposable assembly to the belt. An absorbent article comprising such a belt is also disclosed.

7 Claims, 5 Drawing Sheets

U.S. PATENT DOCUMENTS

| | | | |
|---|---|---|---|
| 2,633,847 A * | 4/1953 | Stringham | 604/402 |
| 2,854,980 A * | 10/1958 | Toellner et al. | 604/402 |
| 2,881,761 A * | 4/1959 | Kenner | 604/397 |
| 3,001,202 A * | 9/1961 | Serrano | 2/102 |
| D191,572 S * | 10/1961 | Hallo | D2/627 |
| 3,227,160 A * | 1/1966 | Younger | 602/79 |
| 3,554,196 A * | 1/1971 | Wargo | 604/402 |
| 3,788,323 A * | 1/1974 | Robinson | 604/399 |
| RE28,483 E * | 7/1975 | Ralph | 604/397 |
| 4,031,897 A * | 6/1977 | Graetz | 604/347 |
| 4,157,719 A * | 6/1979 | DeWoskin | 604/402 |
| 4,231,358 A * | 11/1980 | Atchison | 602/58 |
| 4,695,278 A | 9/1987 | Lawson | |
| 4,710,187 A | 12/1987 | Boland | |
| 4,795,454 A | 1/1989 | Dragoo | |
| D302,626 S * | 8/1989 | Robinson, Jr. | D2/629 |
| 4,964,860 A | 10/1990 | Gipson | |
| 5,074,854 A | 12/1991 | Davis | |
| 5,135,522 A | 8/1992 | Fahrenkrug | |
| 5,212,839 A * | 5/1993 | Sliman et al. | 2/408 |
| 5,275,592 A * | 1/1994 | Grizzaffi | 604/396 |
| 5,445,628 A | 8/1995 | Gipson | |
| 5,685,874 A | 11/1997 | Buell | |
| 5,772,649 A * | 6/1998 | Siudzinski | 604/386 |
| 5,906,604 A | 5/1999 | Rönnberg | |
| 5,971,970 A | 10/1999 | Carlbark | |
| 6,149,637 A * | 11/2000 | Allen et al. | 604/366 |
| 6,336,922 B1 | 1/2002 | Huang et al. | |
| 6,432,099 B2 | 8/2002 | Rönnberg | |
| 6,635,038 B2 * | 10/2003 | Scovel | 604/353 |
| 2003/0018316 A1 * | 1/2003 | Kusibojoska et al. | 604/392 |
| 2003/0097107 A1 * | 5/2003 | Sprengard-Eichel et al. | 604/378 |
| 2004/0030311 A1 | 2/2004 | Suzuki et al. | |
| 2005/0192555 A1 * | 9/2005 | Thomas | 604/402 |

* cited by examiner

WAIST BELT FOR SUPPORTING DISPOSABLE ABSORBENT ASSEMBLIES AND ABSORBENT ARTICLES COMPRISING THE SAME

CROSS REFERENCE TO RELATED APPLICATION

This application claims the benefit of U.S. Provisional Application No. 60/444,272, filed on Jan. 31, 2003.

FIELD OF THE INVENTION

The present invention relates to an absorbent article used for incontinent babies, children or adults, and comprising a waist belt and an absorbent assembly. More particularly, the present invention relates to a reusable waist belt for supporting a disposable absorbent assembly.

BACKGROUND OF THE INVENTION

Disposable absorbent articles worn to assist in the collection of bodily discharges of incontinent persons are well known in the art. Such conventional arts include absorbent articles which comprise a belt for attaching the article around the waist of the wearer. For example, U.S. Pat. No. 5,135,522 issued on Aug. 4, 1992 to Fahrenkrug, et al. discloses a diaper comprising a disposable absorbent chassis assembly and a reusable elasticized belt for attachment of the diaper around the waist of the wearer. The belt disclosed in the Fahrenkrug patent is threaded through fenestrations formed in the side margins of the chassis assembly, and the ends of the belt then engaged with one another around a wearer in order to snugly position the chassis against the wearer's body. Such a structure enables the chassis assembly to firmly be supported by the belt while the diaper is worn. However, the diaper of the patent suffers from the drawback that users or caregivers need to remove the belt from the wearer's body whenever they replace the used chassis assembly with another one.

Another representative belted absorbent article is disclosed in, e.g. U.S. Pat. No. 5,906,604 issued on May 25, 1999 to Rönnberg, et al. It discloses a waist belt for supporting an absorbent garment. In the Rönnberg patent, the belt that is rectangular in shape is worn first so that it encircles around the wearer's waist, and then the belt is fastened in place by the mechanical fastener provided on the belt. Then, one end of the absorbent garment is attached to the outside of the belt on the dorsal waist of the wearer by the hook type fastener provided on the absorbent garment. The other end of the absorbent garment is then passed between the wearer's legs and secured to the outside of the belt on the ventral waist of the wearer by the other hook type fastener provided on the absorbent garment. U.S. Pat. No. 5,971,970 issued on Oct. 26, 1999 to Carlbark, et al. and U.S. Pat. No. 6,432,099B2 issued on Aug. 13, 2002 to Rönnberg also disclose a waist belt for supporting absorbent garments which is similar to that of U.S. Pat. No. 5,906,604.

In such prior arts as described above, the disposable absorbent assembly is attached to the waist belt after the waist belt is worn on the wearer's body. Therefore, users and/or caregivers do not need to expressly remove the belt from the wearer's body when they replace the used absorbent assembly with another one. This results in making the process for exchanging the used absorbent assembly for a new one efficient. However, such conventional waist belts for supporting disposable absorbent assemblies suffer from the drawback that it is difficult for users and/or caregivers to adjust the position of the absorbent assembly on the waist belt at will when they try to attach the absorbent assembly on the waist belt. Such a drawback results from the fact that the conventional waist belts are typically provided in elongated shapes. Because of the elongated shape of the waist belt, the width of the conventional waist belt has not been enough to freely adjust the position of the absorbent assembly on the waist belt. Although one solution on this is to increase the width of the waist belt, the improvident widening of the waist belt can lead to interference of the leg movements of the wearer. In addition, such a merely wide waist belt is apt to be soiled by excreta discharged on the absorbent assembly since it covers the wearer's skin close to the defecation point on the absorbent assembly. This demands users and/or caregivers to frequently exchange the soiled waist belt for a new one. Such a frequent exchange of the waist belt results in increasing the cost of the waist belt for consumers.

Accordingly, there still exists a need for an absorbent article comprising a waist belt and a disposable absorbent assembly which allows users and/or caregivers to easily adjust the position of the absorbent assembly on the waist belt when they attach the disposable assembly on the waist belt. There still remains a need to provide an improved waist belt for supporting a disposable assembly which has a enough attachment area to adjust the position of the disposable assembly on the waist belt without interfering with the leg movements of the wearer, and which is not easily be soiled while the waist belt is worn.

SUMMARY OF THE INVENTION

The waist belt is used for supporting a disposable absorbent assembly. The belt comprises a central segment positioned along the longitudinal centerline of the belt, at least two intermediate segments transversely outwardly extending from the central segment, and at least two distal segments transversely outwardly extending from an intermediate segment. Each intermediate segment covers a side hip of the wearer when the belt is worn. The longitudinal length of each intermediate segment is greater than that of the central segment, and greater than that of each distal segment. The belt further comprises a fastener element positioned on at least one of the distal segments for releasably securing the belt around the waist of the wearer, and an attachment surface formed at least on each intermediate segment for releasably attaching the disposable assembly to the belt.

All documents cited are, in relevant part, incorporated herein by reference; the citation of any document is not to be construed as an admission that it is prior art with respect to the present invention.

BRIEF DESCRIPTION OF THE DRAWINGS

While the Specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION OF THE INVENTION

The definitions of several terms are first provided to assist the reader in understanding the present invention. The term "comprising", as used herein, means that other steps and other ingredients which do not affect the end result can be added. This term encompasses the term "consisting of" and "consisting essentially of". The term "disposable", as used herein, describes devices which generally are not intended to be laundered or otherwise restored or reused (i.e., they are intended to be discarded after a single use and, preferably, to be recycled, composted or otherwise disposed of in an environmentally compatible manner.) The term "excreta" or "bodily discharges", as used herein, are interchangeable, and includes all discharges released from an excretory orifice of a human body, including fecal materials, urine, menses, and the like. The term "excretory orifice", as used herein, refers to an orifice which excreta pass through to discharge the excreta from the human body when excretion occurs. Such an excretory orifice includes urethra, vaginal orifice, anus, and the like. The term "joined" or "joining", as used herein, encompasses configurations in which an element is directly secured to another element by affixing the element directly to the other element; configurations in which the element indirectly secured to the other element by affixing the element to intermediate member(s) which in turn are affixed to the other element; and configurations in which one element is integral with another element, i.e. one element is essentially part of the other element.

Figure 1:
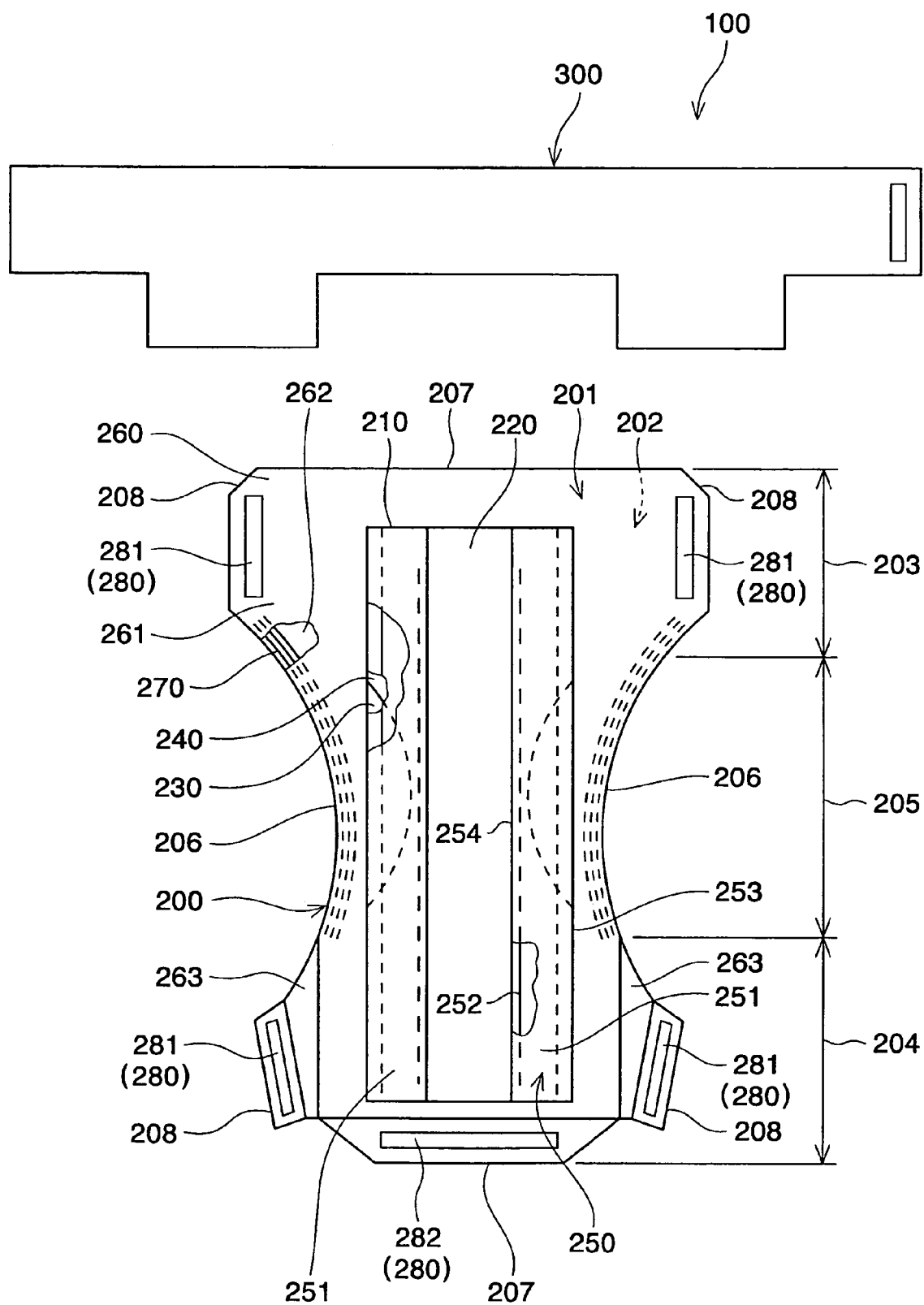
FIG. 1 is a top plan view of one embodiment of an absorbent article of the present invention.
Figure 2:
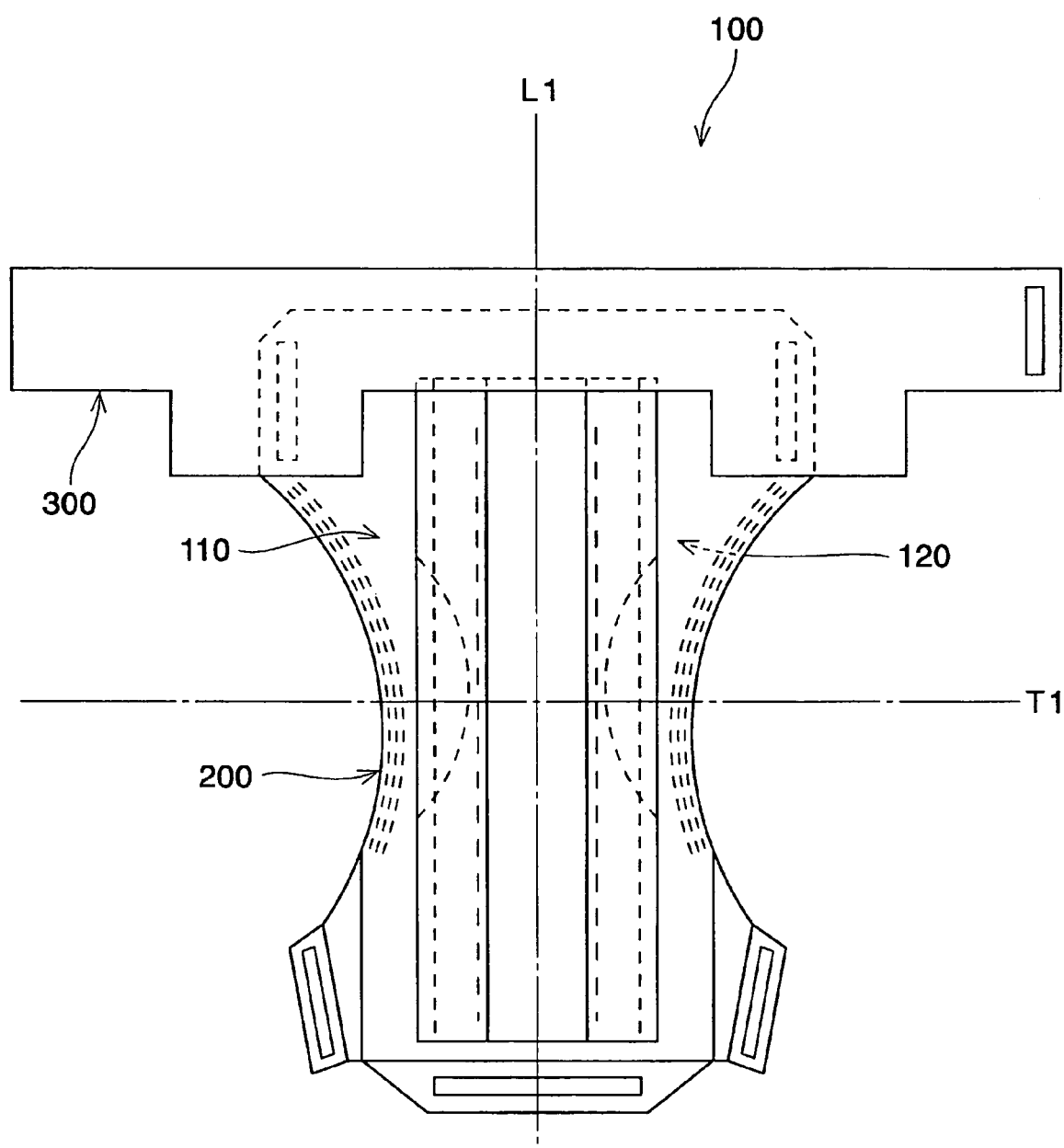
FIG. 2 is a top plan view of the absorbent article of FIG. 1 when the rear region of the disposable assembly is attached to the waist belt.

FIGS. 1 and 2 show one embodiment of an absorbent article of the present invention which is a releasable two-piece absorbent article 100, suitable for use as, but not limited to, an incontinence aid. The term "absorbent article", as used herein, refers to devices which absorb and contain excreta, and more specifically, refers to devices which are placed against or in proximity to the body of the wearer to absorb and contain the various excreta discharged from the body. As used herein, components of the absorbent article 100 are considered "releasable" or "detachable" if the components may be attached and removed more than one time, without destruction or undue distortion of either component. The terms "releasable" and "detachable" are interchangeable with each other. The absorbent article 100 comprises a disposable absorbent assembly 200 and a waist belt 300. The disposable assembly 200 and the waist belt 300 are releasably attached to each other. As shown in FIG. 2, the absorbent article 100 has a longitudinal centerline L1 when the disposable assembly 200 is attached to the waist belt 300. The term "longitudinal", as used herein, refers to a line, axis or direction in the plane of the absorbent article 100 that is generally aligned with (e.g., approximately parallel to) a vertical plane which bisects a standing wearer into left and right body halves when the absorbent article 100 is worn. The absorbent article 100 shown in FIG. 2 also has a transverse centerline T1. The terms "transverse" or "lateral", as used herein, are interchangeable, and refer to a line, axis or direction which lies within the plane of the absorbent article 100 that is generally perpendicular to the longitudinal direction. The absorbent article 100 has two surfaces; one is a wearer-facing surface 110 and the other is an opposing surface 120. The wearer-facing surface 110 is the surface of the article 100 which is generally oriented toward the wearer when the article 100 is worn. The wearer-facing surface 110 typically at least partially comes in contact with the wearer's skin during use of the article 100. The opposing surface 120 is the surface of the article 100 which is generally oriented away from the wearer when the article 100 is worn, and at least partially toward a garment if a garment is worn.

The term "disposable absorbent assembly", as used herein, refers to an assembly typically comprising a liquid pervious topsheet, a liquid impervious backsheet, and an absorbent core in order to acquire and store bodily discharges. Such a disposable assembly may further comprise other features added to form the composite absorbent assembly structure. FIG. 1 shows a top plan view of one embodiment of the disposable absorbent assembly 200 according to the present invention, in its flat-out, uncontracted state (i.e., with elastic induced contraction pulled out) with portions of the structure being cut-away to more clearly show the construction of the disposable assembly 200 and with the portion of the disposable assembly 200 which faces the wearer (i.e., the wearer-facing surface) facing the viewer. As shown in FIG. 1, the disposable absorbent assembly 200 has a wearer-facing surface 201 and a opposing surface 202, a rear region 203, a front region 204 opposed to the rear region 203, and a crotch region 205 positioned between the rear region 203 and the front region 204. The disposable assembly 200 further has a periphery which is defined by side edges 206 and end edges 207. The rear region 203 and the front region 204 extend from the end edges 207 toward the crotch region 205. The disposable absorbent assembly 200 preferably comprises an absorbent unit 210, an outer chassis 260 on which the absorbent unit 210 is disposed, and an attachment means 280 provided on the wearer-facing surface 201 of the disposable absorbent assembly 200.

The absorbent unit 210 comprises a liquid pervious topsheet 220, a liquid impervious backsheet 230, an absorbent core 240 positioned between the topsheet 220 and the backsheet 230. The absorbent unit 210 preferably further comprises a pair of elasticized barrier cuffs 250. The topsheet 220 is preferably positioned so as to be adjacent to the wearer-facing surface of the absorbent core 240 and is preferably joined thereto and to the backsheet 230 by means (not shown) such as those well known in the art. The topsheet 220 and the backsheet 230 may be joined directly to each other. Alternatively, the topsheet 220 and the backsheet 230 may be indirectly joined together by directly joining them to other elements such as the absorbent core 240, the elasticized barrier cuffs 250 and the like by any suitable means known in the art. The backsheet 230 is preferably positioned so as to be adjacent to the opposing surface of the absorbent core 240 and is preferably joined thereto by any suitable means known in the art. While the topsheet 220, the backsheet 230, and the absorbent core 240 may be assembled in a variety of well known configurations in order to form an absorbent unit 210, exemplary assembly configurations are described generally in U.S. Pat. No. 5,074,854; U.S. Pat. No. 4,710,187; and International Patent Publication No. WO 90/04375.

The topsheet 220 is preferably compliant, soft feeling, and non-irritating to the wearer's skin. Further, the topsheet 220 is preferably liquid pervious permitting liquids (e.g., urine) to readily penetrate through its thickness. A suitable topsheet 220 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

The backsheet 230 is to prevent bodily discharges absorbed and contained in the absorbent core 240 from wetting other articles which contact the absorbent article 100 such as bedsheets and undergarments. Thus, the backsheet 230 is preferably impervious to liquids (e.g., urine) and is preferably manufactured from a thin plastic film, although other flexible liquid impervious materials may also be used. However, it is desirable that the backsheet 230 permits vapors to escape from the absorbent article 100. A suitable material for the backsheet 230 is a thermoplastic film having a thickness of from about 0.012 mm (0.5 mil) to about 0.051 mm (2.0 mils), preferably comprising polyethylene or polypropylene.

The absorbent core 240 may be any absorbent member which is capable of absorbing and retaining liquids such as urine and other certain body discharges. The absorbent core 240 may be manufactured in a wide variety of sizes and shapes (e.g., rectangular, hourglass, "T"-shaped, asymmetric, etc.). Preferably, the absorbent core 240 includes a super-absorbent material and a carrier means for the super-absorbent material. In this embodiment, the carrier means is preferably formed from comminuted wood pulp which is generally referred to as airfelt. The configuration and construction of the absorbent core 240 may vary (e.g., the absorbent core may have varying caliper zones, a hydrophilic gradient, a super-absorbent gradient, or lower average density and lower average basis weight acquisition zones; or may comprise one or more layers or structures). Further, the size and absorbent capacity of the absorbent core 240 may also be varied to accommodate wearers ranging from infants through adults.

The absorbent unit 210 preferably further comprises a pair of elasticized barrier cuffs 250 for providing improved containment of liquids and other bodily discharges. The elasticized barrier cuff 250 typically comprises a barrier sheet 251 and an elastic spacing member 252. The elasticized barrier cuff 250 has a fixed edge 253 and a free edge 254. The fixed end 253 is joined to the underlying component, such as the topsheet 220, the backsheet 230, the absorbent core 240, and the like, by means (not shown) such as those well known in the art. The elastic spacing member 252 is enclosed by the barrier sheet 251 such that the elastic spacing member 252 is adjacent to the free edge 254 of the elastic barrier cuff 250. The elastic spacing member 252 allows the free edge 254 of the barrier cuff 250 to stand up away from the topsheet 220 in the crotch region 205 of the disposable absorbent assembly 200. While such an elasticized barrier cuff may comprise several different embodiments for reducing the leakage of bodily discharges, exemplary structures are described generally in U.S. Pat. No. 4,695,278; U.S. Pat. No. 4,795,454; and U.S. Pat. No. 5,685,874.

The outer chassis 260 may be joined with at least a portion of the opposing surface of backsheet 230 to support the absorbent unit 210 on its wearer-facing surface. Alternatively, the outer chassis 260 may be omitted if the absorbent disposable assembly 200 comprises only the absorbent unit 210. The outer chassis 260 has a periphery which is defined by side edges and end edges. In the embodiment shown in FIG. 1, the side edges and the end edges of the outer chassis 260 correspond to the side edges 206 and the end edges 207 of the disposable absorbent assembly 200 respectively. The outer chassis 260 can comprise one or multiple layers, preferably two or three layers. In the embodiment shown in FIG. 1, the outer chassis 260 comprises two layers, which comprises a wearer-facing layer 261 and an opposing layer 262. The wearer-facing layer 261 is positioned on the wearer-facing surface of the outer chassis 260, and typically at least partially contacts with the wearer's skin when the absorbent article 100 is worn. The opposing layer 262 is positioned on the opposing surface of the outer chassis 260, and typically at least partially contacts with the garments of the wearer if a garment is worn. The outer chassis 260 further comprises one or more elastic strands 270 adjacent to the side edge 206 for providing the fit of the disposable assembly 200 around the wearer's leg while the absorbent article 100 is worn. This also results in preventing leakage of bodily discharges out of the side edge 206 while the absorbent article 100 is worn. In addition, the outer chassis 260 preferably comprises one or more elasticized zones 263. The elasticized zone 263 is intended to elastically expand and contract such that the disposable assembly 200 dynamically fits the wearer' body during use of the absorbent article 100. As shown in FIG. 1, the elasticized zone 263 is preferably adjacent to the attachment means 280. The outer chassis 260 preferably comprises a nonwoven material. Alternatively, the outer chassis 260 may comprise materials such as woven webs, scrims, films, loose fibers, or any other material or combination of materials known in the art. If the outer chassis 260 comprises two layers, i.e., the wearer-facing layer 261 and the opposing layer 262, the layers may comprise any material such as a nonwoven or a polymeric film. In a preferred embodiment, the layers may be formed from a laminate comprising two nonwoven layers, or a nonwoven layer and a polymeric film.

The attachment means 280 provided on the wearer-facing surface 201 of the disposable assembly 200 functions to attach the disposable absorbent assembly 200 on the opposing surface of the waist belt 300. In a preferred embodiment, the attachment means 280 is one or more patches of hook type material which is complementary to the opposing surface of the waist belt 300. Alternatively, the attachment means 280 may be one or more patches of receiving material if the opposing surface of the waist belt 300 comprises hook type material. The term "hook type material", as used herein, refers to any material having a fastening system joined to and projecting from a substrate. The fastening system may have one or more mechanical engaging means which project, typically radially, from a shank which is joined to the substrate. The engaging means is typically the portion of the hook type material which penetrates and is secured to the exposed surface of the complementary receiving material. Suitable hook type material is sold by the Minnesota Mining and Manufacturing Company of Minneapolis, Minn. as Model Number XPO-0040 and by Velcro U.S.A., Inc. of Manchester, N.H. as Hook 88. The term "receiving material", as used herein, refers to any material having an exposed surface with tightly spaced openings complementary to the hook type material. Such openings are typically defined by one or more strands or fibers. The complementary hook type material may be entrapped by the exposed surface of the receiving material, and may not be withdrawn without interference. For the embodiment described herein, loop material having a pile depth of about 0.8 millimeters works well as a receiving material. Hook type material and receiving material are considered "complementary" if the openings between the strands or fibers are sized to allow at least one engaging means of the hook type material to penetrate into the exposed surface of the receiving material and to be engaged or intercepted thereby. Preferably, patches 281 may be disposed on the wearer-facing surface 201 of the disposable assembly 200 such that each of the patches 281 is adjacent to each of the four corners 208 of the disposable assembly 200 as shown in FIG. 1. More preferably, besides the patches 281 provided on the corners 208, an additional patch 282 may be disposed on the wearer-facing surface 201 of the disposable assembly 200 such that the patch 282 is adjacent to the end edge 207 in the front region 204. Such an additional patch may also be disposed so as to be adjacent to the end edge 207 in the rear region 203. The patches 281, 282 may be joined to the disposable assembly 200 by any means well known in the art such that the joining strength exceeds the desired peel and shear strength. While the patches 281, 282 are disposed on the wearer-facing surface of the outer chassis 260 in the embodiment shown in FIG. 1, the patches 281, 282 may also be disposed on the wearer-facing surface of the absorbent unit 210. In another embodiment (not shown), the attachment means 280 may be one or more patches of adhesive instead of patches of hook or loop type material. Suitable adhesive is sold by Eastman Chemical Products Company of Kingsport, Tenn. under the tradename Eastobond A-3. If adhesive patches are selected as the attachment means 280, the waist belt 300 should be adapted to provide a complementary attachment surface to which such adhesive patches will readily adhere. A polyethylene material is suitable for providing the waist belt 300 with such a complementary attachment surface.

The waist belt 300 is the component of the absorbent article 100 to which the disposable absorbent assembly 200 is attached. The waist belt 300 encircles the waist of the wearer, and supports the disposable assembly 200 while the absorbent article 100 is worn. The waist belt 300 is preferably reusable, and is not intended to be soiled by the collection of bodily discharges. The waist belt 300 is also intended to be worn when the absorbent core 240 becomes loaded by such bodily discharges. The term "reusable", as used herein, refers to an absorbent article, or component thereof, intended to be laundered and restored rather than to be discarded after single use. The waist belt 300 should be clean in appearance, nonirritating to the skin of the wearer, and able to accommodate a wide range of wearer sizes. Although not required, it may be desirable to have one waist belt 300 matched to a given wearer over a period of time, or, alternatively and particularly for institutional use, such a waist belt 300 may be laundered, sanitized and interchanged among various wearers. The waist belt 300 is designed to having sufficient strength in order to resist rupturing in use, e.g., when force to the waist belt 300 is exerted in typical wearing condition such as sitting, walking, or the like. In a preferred embodiment, the waist belt 300 may be made from a unitary piece of material. Alternatively, the waist belt 300 may be made from a number of separate pieces of material which may be identical or different and which are joined to one another. The waist belt 300 can comprise one or multiple layers, preferably two or three layers. The layer of the waist belt 300 may comprise any material such as a nonwoven, a polymeric film, a woven web, scrim, or any other material or combination of materials known in the art. In a preferred embodiment, such a layer may be formed from a laminate comprising two nonwoven layers, or a nonwoven layer and a polymeric film. The layer positioned on the wearer-facing surface 301 of the waist belt 300 is preferably provided with a nonwoven layer. Such a nonwoven layer presents a compliant surface to the skin of a wearer and thus greatly improves skin healthiness. The waist belt 300 may also comprise three layers; one film layer and two nonwoven layers. Preferably, the film may be interposed between the two nonwoven layers. This sequence of layers results in a closed fibrous structure, which has a particularly pleasing sensation on contact with the skin of a wearer. The nonwoven layer or the nonwoven layers constituting the waist belt 300 may be hydrophobic or hydrophilic.

Figure 3:
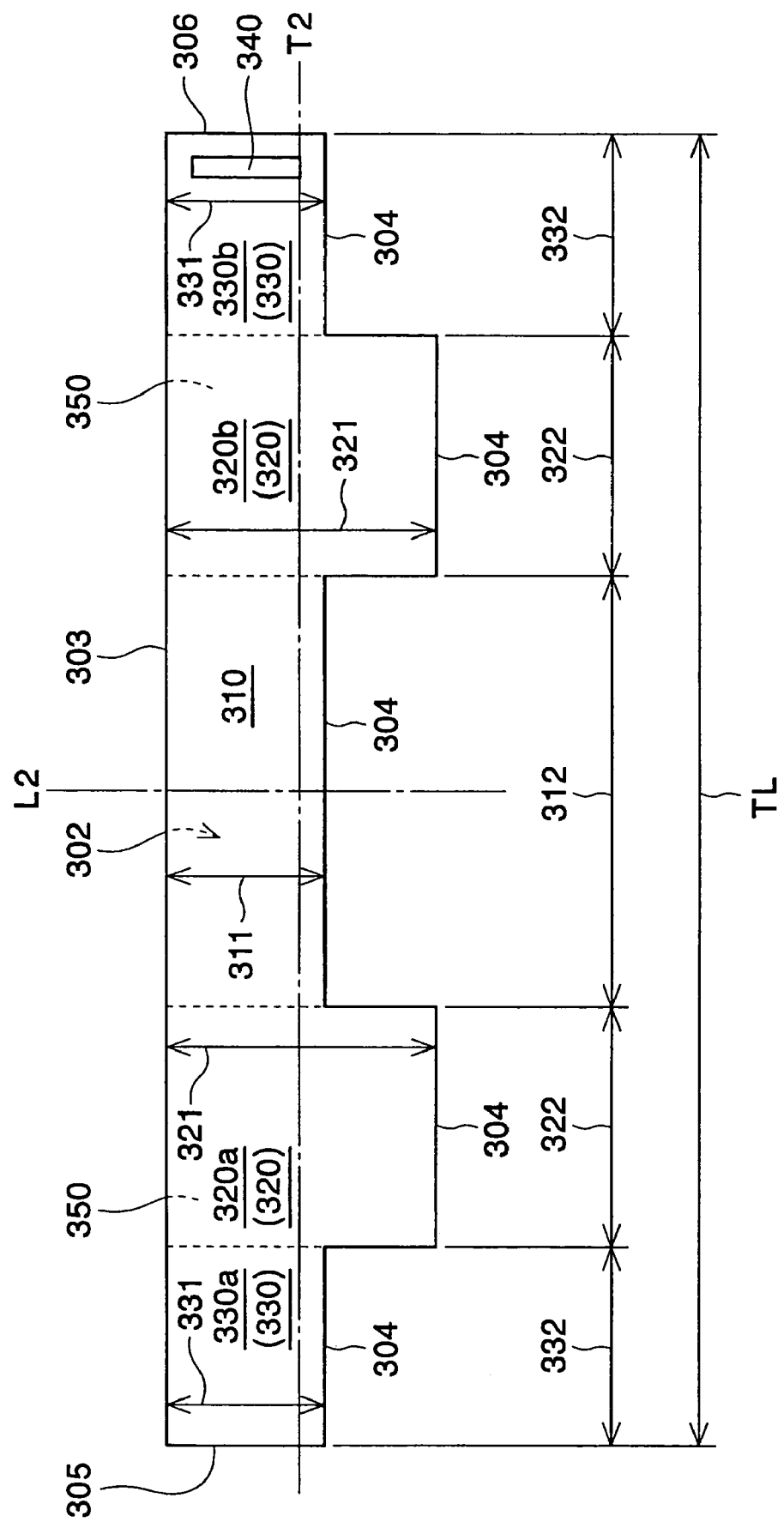
FIG. 3 is a top plan view of one embodiment of a waist belt of the present invention.

FIG. 3 shows a preferred embodiment of the waist belt 300 according to the present invention which is used for supporting the disposable assembly 200, in its flat-out, uncontracted state with the portion of the waist belt 300 which faces the wearer (i.e., the wearer-facing surface) facing the viewer. The waist belt 300 shown in FIG. 3 has a longitudinal centerline L2 and a transverse centerline T2 which is perpendicular to the longitudinal centerline L2. The term "longitudinal", when used for the waist belt 300, refers to a line, axis or direction in the plane of the waist belt 300 that is substantially parallel, preferably corresponding, to the longitudinal direction L1 of the absorbent article 100 when the disposable assembly 200 is attached to the waist belt 300 as shown in FIG. 2. The terms "transverse" or "lateral", when used for the waist belt 300, refer to a line, axis or direction in the plane of the waist belt 300 that is generally perpendicular to the longitudinal direction. The waist belt 300 has two surfaces; one is a wearer-facing surface 301 and the other is an opposing surface 302. The waist belt 300 further has two end edges 303, 304 oppositely disposed with respect to the transverse centerline T2, and two side edges 305, 306 oppositely disposed with respect to the longitudinal centerline L2. The waist belt 300 comprises a central segment 310, at least two intermediate segments 320 (320a, 320b) and at least two distal segments 330 (330a, 330b). The waist belt 300 further comprises a fastener element 340 as shown in FIG. 3. The waist belt 300 may be provided in any size depending on the wearer group for which the waist belt 300 is intended. The transverse length of the waist belt 300 is measured along the transverse centerline T2. The waist belt may have a transverse length TL of between about 125 mm and about 1600 mm, preferably between about 500 mm and about 1300 mm, if the waist belt 300 is designed for adult wearers. In addition, the waist belt 300 may have a transverse length TL of between about 50 mm and about 700 mm, preferably between about 200 mm and about 500 mm, if the waist belt 300 is designed for infant wearers. As for the longitudinal length of the waist belt 300, it will be described below.

The central segment 310 is positioned along the longitudinal centerline L2 and extends transversely outwardly from the longitudinal centerline L2 in either side of the longitudinal centerline L2. The central segment 310 has a first longitudinal length 311 which is defined by the distance between the end edges 303, 304 of the central segment 310. The central segment 310 may preferably cover the dorsal waist of the wearer when the waist belt 300 is worn. Alternatively, the waist belt 300 may also be worn such that the central segment 310 covers the ventral waist of the wearer. The central segment 310 may be elasticized partially and wholly by means (not shown) such as those well known in the art so as to elastically expand and contract, especially if the central segment 310 covers the dorsal waist of the wearer when the waist belt 300 is worn. Such elasticized central segment 310 helps the waist belt 300 dynamically fit the wearer' body while the waist belt 300 is worn. The first longitudinal length 311 of the central segment 310 is measured along the longitudinal centerline L2. The first longitudinal length 311 may be between about 5 mm and about 250 mm, preferably between about 50 mm and about 100 mm, if the waist belt 300 is designed for adult wearers. In addition, the first longitudinal length 311 may be between about 5 mm and about 100 mm, preferably between about 30 mm and about 50 mm, if the waist belt 300 is designed for infant wearers. The central segment 310 may also have transverse length 312. The transverse length 312 of the central segment 310 is measured along the transverse centerline T2 as shown in FIG. 3. The central segment 310 may have a transverse length 312 of between about 50 mm and about 500 mm, preferably between about 100 mm and about 300 mm, if the waist belt 300 is designed for adult wearers. In addition, the central segment 310 may have a transverse length 312 of between about 20 mm and about 200 mm, preferably between about 50 mm and about 100 mm, if the waist belt 300 is designed for infant wearers.

Each intermediate segment 320a, 320b transversely outwardly extends from the central segment 310 and is positioned between the central segment 310 and the distal segment 330. Each intermediate segment 320a, 320b covers a side hip of the wearer when the waist belt 300 is worn. Each intermediate segment 320 has a second longitudinal length 321 which is defined by the distance between the end edges 303, 304 of each intermediate segment 320a, 320b. The intermediate segment 320 may be elasticized partially and wholly by means (not shown) such as those well known in the art so as to elastically expand and contract. Such elasticized intermediate 320 segment helps the waist belt 300 dynamically fit the wearer's body while the waist belt 300 is worn. In particular, it is preferable that at least the end edge 304 of the intermediate segment 320 is elasticized. Such an elasticized end edge 304 of the intermediate segment 320 provides the improved fit of the absorbent article 100 around the wearer's leg in cooperation with the elastic strands 270 provided along the side edge 206 of the disposable assembly 200. The second longitudinal length 321 of the intermediate segment 320 is measured along the longitudinal centerline L2. The second longitudinal length 321 may be between about 30 mm and about 400 mm, preferably between about 100 mm and about 250 mm, if the waist belt 300 is designed for adult wearers. In addition, the second longitudinal length 321 may be between about 20 mm and about 200 mm, preferably between about 50 mm and about 100 mm, if the waist belt 300 is designed for infant wearers. The intermediate segment 320 may also have transverse length 322. The transverse length 322 of the intermediate segment 320 is measured along the transverse centerline T2 as shown in FIG. 3. The intermediate segment 320 may have a transverse length 322 of between about 50 mm and about 500 mm, preferably between about 100 mm and about 300 mm, if the waist belt 300 is designed for adult wearers. In addition, the intermediate segment 320 may have a transverse length 322 of between about 20 mm and about 200 mm, preferably between about 50 mm and about 100 mm, if the waist belt 300 is designed for infant wearers.

Each distal segment 330a, 330b extends transversely outwardly from the corresponding intermediate segment 320 and includes one of the side edges 305, 306 of the waist belt 300. Each distal segment 330a, 330b has a third longitudinal length 331 which is defined by the distance between the end edges 303, 304 of each distal segment 330a, 330b. The distal segment 330 may preferably cover the ventral waist of the wearer when the waist belt 300 is worn. Alternatively, the waist belt 300 may also be worn such that the distal segment 330 covers the dorsal waist of the wearer. The distal segment 330 may be elasticized partially and wholly by means (not shown) such as those well known in the art so as to elastically expand and contract, especially if the distal segment 330 covers the dorsal waist of the wearer when the waist belt 300 is worn. Such elasticized distal segment 330 helps the waist belt 300 dynamically fit the wearer' body while the waist belt 300 is worn. The third longitudinal length 331 of the distal segment 330 is measured along the longitudinal centerline L2. The third longitudinal length 331 may be between about 5 mm and about 250 mm, preferably between about 50 mm and about 100 mm, if the waist belt 300 is designed for adult wearers. In addition, the third longitudinal length 331 may be between about 5 mm and about 100 mm, preferably between about 30 mm and about 50 mm, if the waist belt 300 is designed for infant wearers. The distal segment 330 may also have transverse length 332. The transverse length 332 of the distal segment 330 is measured along the transverse centerline T2 as shown in FIG. 3. The distal segment 330 may have a transverse length 332 of between about 20 mm and about 300 mm, preferably between about 50 mm and about 150 mm, if the waist belt 300 is designed for adult wearers. In addition, the distal segment 330 may have a transverse length 332 of between about 20 mm and about 150 mm, preferably between about 30 mm and about 80 mm, if the waist belt 300 is designed for infant wearers.

Figure 4:
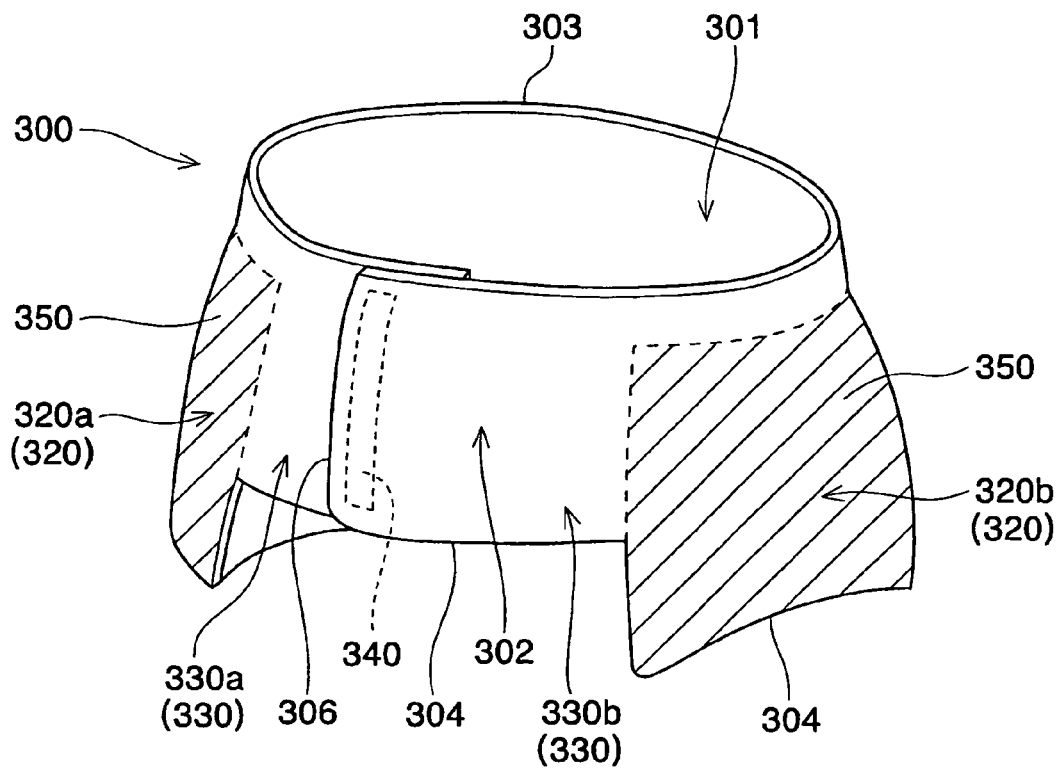
FIG. 4 is a schematic perspective view of the waist belt shown in FIGS. 1 to 3 when the waist belt is worn.
Figure 5:
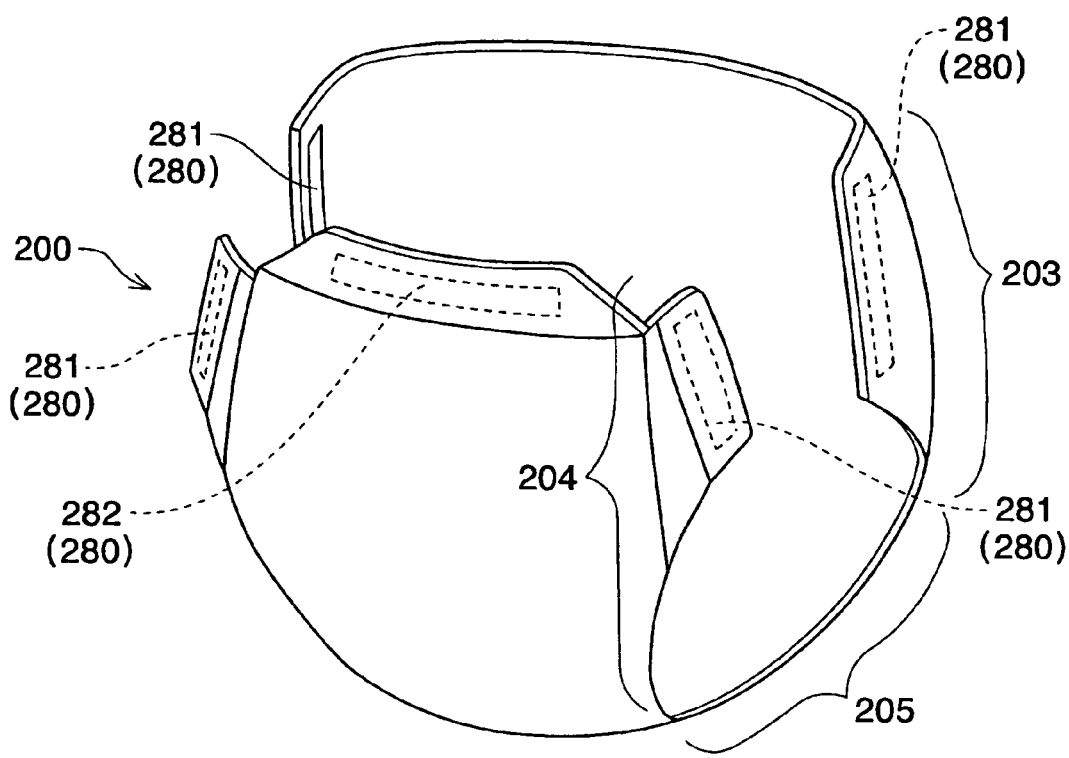
FIG. 5 is a schematic perspective view of the disposable absorbent assembly shown in FIGS. 1 and 2 when the disposable absorbent assembly is worn.
Figure 6:
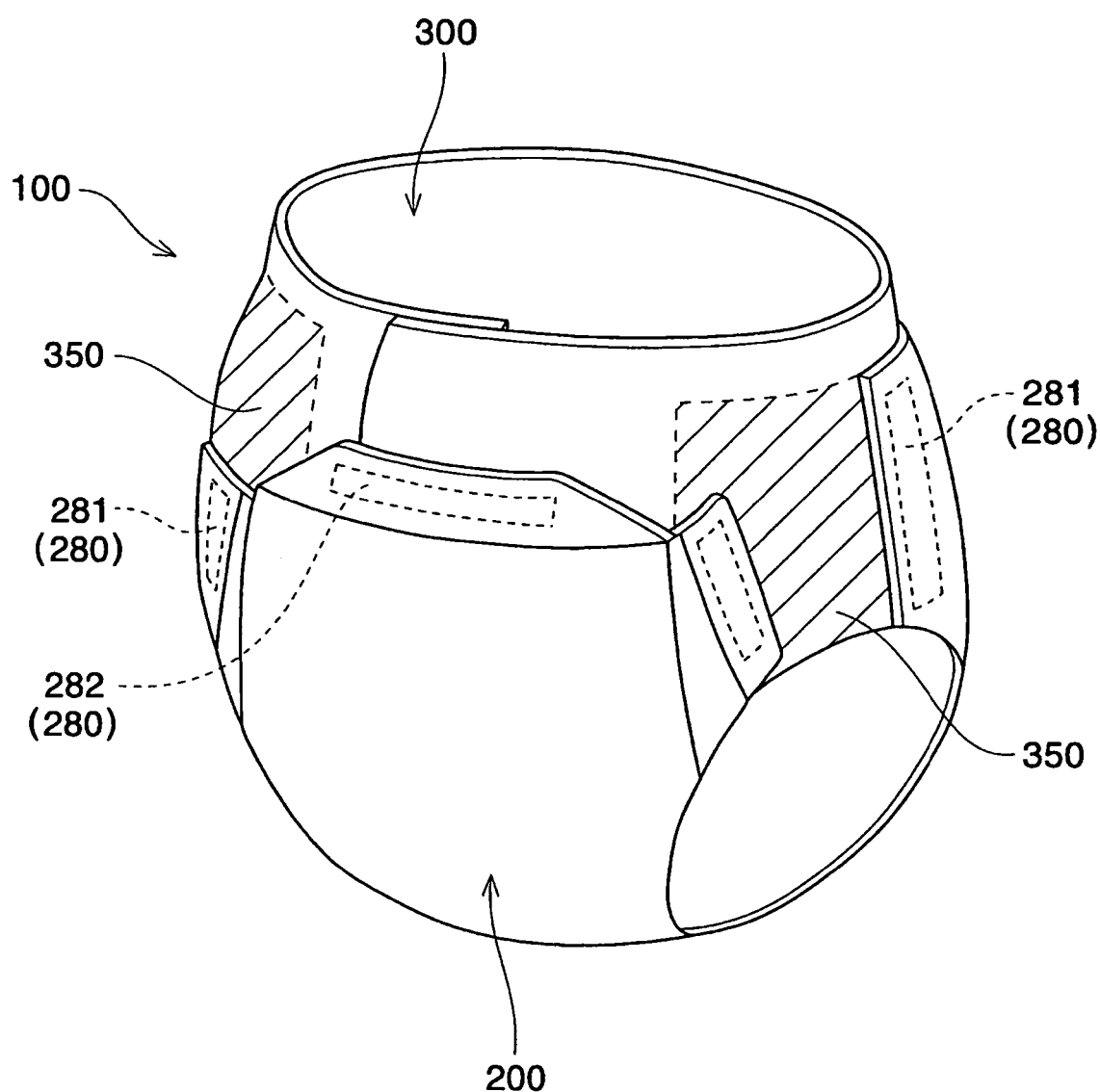
FIG. 6 is a schematic perspective view of the absorbent article when the absorbent article is worn.

According to the present invention, the second longitudinal length 321 of each intermediate segment 320a, 320b is greater than the first longitudinal length 311 of the central segment 310, and greater than the third longitudinal length 331 of each distal segment 330a, 330b. In addition, an attachment surface 350 is formed at least on the opposing surface 302 of each intermediate segment 320a, 320b of the waist belt 300 for releasably attaching the disposable assembly 200 to the belt 300 as shown by the shaded portions in FIG. 4. Each attachment surface 350 is complementary to the attachment means 280 of the disposable assembly 200 for releasably attaching the disposable assembly 200 to the waist belt 300. The perspective views of the waist belt 300 and the disposable assembly 200 when they are worn are schematically shown in FIGS. 4 and 5 respectively, and further the perspective view of the absorbent article 100 when the waist belt 300 supports the disposable assembly 200 is schematically shown in FIG. 6. As shown in FIGS. 4 to 6, the patches 281 are positioned on the rear region 203 and the front region 204 of the disposable assembly 200 such that the patches 281 are complementarily attached on the attachment surfaces 350 of the waist belt 300 when the absorbent article 100 is worn. In the typical placement of the absorbent article 100 of the present invention, the waist belt 300 is fastened around the waist of the wearer first by attaching the fastener element 340 provided on the wearer-facing surface 301 of the waist belt 300 to the opposing surface 302 of the waist belt 300. The patches 281 provided on the rear region 203 of the disposable assembly 200 are then attached to the attachment surface 350 of each intermediate segment 320a, 320b of the waist belt 300. Subsequently, the front region 204 of the disposable assembly 200 is brought forwards through the wearer's crotch, and finally the patches 281 provided on the front region 203 of the disposable assembly 200 are attached to the attachment surface 250 of each intermediate segment 320a, 320b of the waist belt 300 as shown in FIG. 6. Because the second longitudinal length 321 of the intermediate segment 320 is greater than the first and third longitudinal lengths 311, 331 of the central and distal segments 310, 330, the waist belt 300 of the present invention provides an enough attachment area to adjust the position of the disposable assembly 200 on the waist belt 300 (especially in the longitudinal direction). This provides the advantage that the absorbent article 100 of the present invention is applicable to wearers of various sizes. According to the absorbent article 100 of the present invention, it is possible for users and/or caregivers to easily adjust the position of the disposable assembly 200 on the waist belt 300 without taking off the waist belt 300 from the wearer even after the disposable assembly 200 is attached on the waist belt 300 secured around the waist of the wearer. Since the waist belt 300 of the present invention provides an enough attachment area (i.e., the attachment surface 350 of each intermediate segment 320a, 320b) to which the attachment means 280 of the disposable assembly 200 is complementarily attached, it is possible to additionally dispose another absorbent article such as a supplemental absorbent pad having various sizes on the disposable assembly 200 when the absorbent article 100 is worn. Such a longitudinally longer intermediate segment 320 in contrast with the central and distal segments 310, 330 efficiently prevents the waist belt 300 from twisting during use of the belt 300 in spite of the fact that the central and distal segments 310, 330 are longitudinally short. This is because the intermediate segment 320 widely contacts with and covers the wearer's body. In addition, the waist belt 300 of the present invention hardly interferes with the leg movements of the wearer while the waist belt 300 is worn since the central and distal segments 310, 330 are longitudinally shorter than the intermediate segment 320. Such longitudinally shorter central and distal segments 310, 330 in contrast with the intermediate segment 320 are hardly soiled by bodily discharges which are discharged to the disposable assembly 200 because the end edges 304 of the central and distal segments 310, 330 are distantly positioned from the excretory orifice of the wearer. Preferably, the attachment surface 350 may be formed on the opposing surface 302 of the distal segment 330 besides the intermediate segment 320 if the waist belt 300 is worn such that the distal segment 330 covers the ventral waist of the wearer. Alternatively, the attachment surface 350 may be formed on the opposing surface 302 of the central segment 310 besides the intermediate segment 320 if the waist belt 300 is worn such that the central segment 330 covers the ventral waist of the wearer. Such an attachment surface 350 formed on the distal segment 330 or the central segment 310 enables the above-mentioned additional patch 282 adjacent to the end edge 207 of the disposable assembly 200 to be secured on the opposing surface 302 of the waist belt 300 for more secure attachment between the disposable assembly 200 and the waist belt 300. The attachment surface 350 may be integral with the opposing surface 302 of the waist belt 300, or may be a separate element attached to the opposing surface 302 of the waist belt 300. Suitable materials for the attachment surface 350 of the waist belt 300 have been described above with respect to, e.g., hook type material, receiving material or complementary attachment surface to which adhesive patches adhere, for the attachment means 280 of the disposable assembly 200. In a preferred embodiment, the attachment surface 350 may comprise the receiving material sold by KURARAY Co. as Model Number CX-780.

The fastener element 340 is positioned on one of the distal segments 330a, 330b of the waist belt 300 for releasably securing the waist belt 300 around the waist of the wearer. The fastener element 340 is preferably disposed on the wearer-facing surface 301 of one of the distal segments 330a, 330b such that the fastener element 340 is adjacent to the side edge 305 or 306 of the waist belt 300. In the embodiment shown in FIG. 3, the fastener element 340 is disposed so as to be adjacent to the side edge 306 of the distal segment 330. As shown in FIG. 4, the waist belt 300 is secured around the waist of the wearer by attaching the fastener element 340 to the opposing surface 302 of the waist belt 300. The fastener element 340 is preferably one or more patches of hook type material which is complementary to the opposing surface 302 of the waist belt 300. Alternatively, the fastener element 340 may be one or more patches of receiving material if the opposing surface 302 of the waist belt 300 comprises hook type material. In another embodiment, the fastener element 340 may be disposed on the opposing surface 302 of the waist belt 300 if the fastener element 340 is complementary to the wearer-facing surface 301 of the waist belt 300. The fastener element 340 may be joined to the wearer-facing surface 301 or the opposing surface 302 of the waist belt 300 by any means well known in the art such that the joining strength exceeds the desired peel and shear strength. In another embodiment (not shown), the fastener element 340 may be one or more patches of adhesive instead of patches of hook or loop type material. If adhesive patches are selected as the fastener element 340, a complementary attachment surface to which such adhesive patches will readily adhere should be provided on the wearer-facing surface 301 or the opposing surface 302 of the waist belt 300.

The disposable assembly 200 is attached to the waist belt 300 such that the attachment surface 350 of the waist belt 300 and the attachment means 280 of the disposable assembly 200 should interact to resist a peel force occurring while the article 100 is worn. The term "peel force", as used herein, refers to forces to separate one component of the absorbent article 100 from another component of the article 100 when such components are attached to each other. In addition, the attachment means 280 of the disposable assembly 200 should be releasably attached to the attachment surface 350 of the waist belt 300 while the attachment of the disposable assembly 200 to the waist belt 300 resists the peel force described above. Therefore, the peel force of the attachment means 280 of the disposable assembly 200 to the attachment surface 350 of the waist belt 300 should not be too great since the attachment means 280 and/or the attachment surface 350 may tear when the attachment means 280 is removed from the attachment surface 350. Thus, the attachment means 280 of the disposable assembly 200 to the attachment surface 350 of the waist belt 300 should be preferably between about 0.5 N/cm and about 10 N/cm, more preferably between about 2 N/cm and about 3 N/cm.

The following method describes the procedure for measuring the peel force, in N/cm, of the combined the material of the attachment means 280 of the disposable assembly 200 and the attachment surface 350 of the waist belt 300. A suitable instrument used for the measurement of the peel force for the attachment means 280 of the disposable assembly 200 and the attachment surface 350 of the waist belt 300 is INSTRON 5564 which may be equipped with either digital readout or strip chart data display for load and elongation. The following procedure is conducted under standard laboratory conditions at 23° C. (73° F.) and 50% relative humidity for a minimum of 2.0 hours.

(1) Cut a material of the attachment means 280 into a strip having 25 mm by 90 mm size to make Sample A, and a material of the attachment surface 350 into a strip having 50 mm by 100 mm size to make Sample B.

(2) Attach Sample A on Sample B to make a sample strip such that they are wholly overlapped with each other. At least 3 sample strips should be prepared for the measurement.

(3) Roll a rubber coated steel roller of diameter of 95 mm, a width of 45 mm and a weight of 2 kg, forth and back on the sample strip in the length direction of the sample strip once (a total of two passes).

(4) Put the sample strip in the instrument. The way to set the sample strip is to insert the non-attached end of Sample A into the top clamp of the instrument first, and then to insert the non-attached end of Sample B into the bottom clamp with enough tension to eliminate any slack of the sample strip.

(5) Peel Sample A of the sample strip from Sample B of the sample strip at a peeling speed of 300 mm/minute until completely separating them from each other.

(6) Read the peel force values in a peeling range between 5 mm and 25 mm (i.e., a change of the distance between the top clamp and the bottom clamp).

(7) Read the peak value of the peel force values which are read in the procedure (6).

(8) Repeat the above procedures (1) to (7) for the other sample strips.

(9) Calculate the Peel Force as follows:

Peel Force=Sum of the peak peel force values of the procedure (7) for samples tested/(N/cm) Number of test strips tested Attachment of the attachment means 280 of the disposable assembly 200 to the attachment surface 350 of the waist belt 300 according to the particular peel force parameters given above results in a product with increased effectiveness. For example, if the peel force of the attachment means 280 to the attachment surface 350 is less than the particular peel force given above, the attachment means 280 of the disposable assembly 200 will easily come off from the attachment surface 350 of the waist belt 300 while the absorbent article 100 is worn. This may result in leakage of bodily discharges contained into the disposable assembly 200 during use of the absorbent article 100. In contrast, if the peel force of the attachment means 280 to the attachment surface 350 is greater than the particular peel force given above, it is difficult for users and/or caregivers to remove the attachment means 280 of the disposable assembly 200 from the attachment surface 350 of the waist belt 300. In such a case, if the user/caregiver forcibly tries to remove the attachment means 280 of the disposable assembly 200 from the attachment surface 350 of the waist belt 300, the attachment means 280 of the disposable assembly 200 and/or the attachment surface 350 of the waist belt 300 may even tear.

What is claimed is:

1. A waist belt for supporting a disposable absorbent assembly, the belt having a longitudinal centerline, a transverse centerline, a wearer-facing surface, an opposing surface, two end edges oppositely disposed with respect to the transverse centerline, and two side edges oppositely disposed with respect to the longitudinal centerline;

the belt comprising a central segment, at least two intermediate segments and at least two distal segments;

the central segment being positioned along the longitudinal centerline and extending transversely outwardly from the longitudinal centerline on either side of the longitudinal centerline, the central segment having a first longitudinal length defined by the distance between the end edges of the central segment;

each intermediate segment transversely outwardly extending from the central segment and being positioned between the central segment and a distal segment, each intermediate segment covering a side hip of the wearer when the belt is worn, each intermediate segment having a second longitudinal length defined by the distance between the end edges of each intermediate segment;

each distal segment extending transversely outwardly from an intermediate segment and including one of the side edges of the belt, each distal segment having a third longitudinal length defined by the distance between the end edges of each distal segment;

wherein the second longitudinal length is greater than the first longitudinal length, and greater than the third longitudinal length;

wherein the belt comprises a fastener element positioned on at least one of the distal segments for releasably securing the belt around the waist of the wearer, and an attachment surface formed at least on the opposing surface of each intermediate segment for releasably attaching the disposable assembly to the belt; and wherein the attachment surface for releasably attaching the absorbent assembly to the belt is formed on the opposing surfaces of the intermediate segments and the central segment.

2. A waist belt according to claim 1 wherein the attachment surface for releasably attaching the absorbent assembly to the belt is formed on the opposing surfaces of the intermediate segments and the distal segments.

3. A waist belt according to claim 1 wherein the second longitudinal length of the intermediate segment is between 100 mm and 250 mm if the belt is designed for adult wearers.

4. A waist belt according to claim 1 wherein the second longitudinal length of the intermediate segment is between 50 mm and 100 mm if the belt is designed for infant wearers.

5. An absorbent article having a longitudinal centerline, a transverse centerline, a wearer-facing surface and an opposing surface;

the absorbent article comprising:

a disposable absorbent assembly comprising a liquid pervious topsheet, a liquid impervious backsheet, an absorbent core positioned between the topsheet and the backsheet, and an attachment means provided on the wearer-facing surface of the disposable assembly;

a waist belt having two end edges oppositely disposed with respect to the transverse centerline, and two side edges oppositely disposed with respect to the longitudinal centerline, the belt comprising a central segment, at least two intermediate segments and at least two distal segments;

the central segment being positioned along the longitudinal centerline and extending transversely outwardly from the longitudinal centerline on either side of the longitudinal centerline, the central segment having a first longitudinal length defined by the distance between the end edges of the central segment;

each intermediate segment transversely outwardly extending from the central segment and being positioned between the central segment and a distal segment, each intermediate segment covering a side hip of the wearer when the belt is worn, each intermediate segment having a second longitudinal length defined by the distance between the end edges of each intermediate segment;

each distal segment extending transversely outwardly from an intermediate segment and including one of the side edges of the belt, each distal segment having a third longitudinal length defined by the distance between the end edges of each distal segment;

wherein the second longitudinal length is greater than the first longitudinal length, and greater than the third longitudinal length;

wherein the belt comprises a fastener element positioned on at least one of the distal segments for releasably securing the belt around file waist of the wearer, and an attachment surface formed at least on the opposing surface of each intermediate segment of the belt such that the attachment surface is complementary to the attachment means for releasably attaching the disposable assembly to the belt; and wherein the attachment surface for releasably attaching the absorbent assembly to the belt is formed on the opposing surfaces of the intermediate segments and the central segment.

6. An absorbent article according claim 5 wherein the second longitudinal length of the intermediate segment is between 100 mm and 250 mm if the belt is designed for adult wearers.

7. An absorbent article according claim 5 wherein the second longitudinal length of the intermediate segment is between 50 mm and 100 mm if the belt is designed for infant wearers.

* * * * *

UNITED STATES PATENT AND TRADEMARK OFFICE
CERTIFICATE OF CORRECTION

| | |
|---|---|
| PATENT NO. | : 7,211,072 B2 |
| APPLICATION NO. | : 10/768949 |
| DATED | : May 1, 2007 |
| INVENTOR(S) | : Noriko Nawata et al. |

It is certified that error appears in the above-identified patent and that said Letters Patent is hereby corrected as shown below:

Column 15

Line 11, delete "file" and insert -- the --.

Signed and Sealed this

Thirty-first Day of July, 2007

JON W. DUDAS
*Director of the United States Patent and Trademark Office*